United States Patent [19]

Westcott

[11] Patent Number: 5,501,972

[45] Date of Patent: Mar. 26, 1996

[54] **METHOD OF PRODUCING EMBRYOGENIC CALLUS OF NORWAY SPRUCE (*PICEA ABIES* AND REGENERATING PLANTLETS THEREFROM**

[75] Inventor: Roger J. Westcott, Wellingborough, United Kingdom

[73] Assignee: Unilever Patent Holdings B.V., Vlaardingen, Netherlands

[21] Appl. No.: 187,818

[22] Filed: Jan. 27, 1994

Related U.S. Application Data

[63] Continuation of Ser. No. 898,903, Jun. 10, 1992, abandoned.

[51] Int. Cl.⁶ ............................... C12N 5/04; C12N 5/02; C12N 5/00
[52] U.S. Cl. ............................... 435/240.49; 435/240.48; 435/240.45; 435/240.4
[58] Field of Search ........................... 435/240.4, 240.45, 435/240.47, 240.48, 240.49; 800/DIG. 49

[56] References Cited

FOREIGN PATENT DOCUMENTS

| | | |
|---|---|---|
| 263017 | 6/1988 | European Pat. Off. . |
| 2626285 | 1/1988 | France . |
| 2231585 | 11/1990 | United Kingdom . |
| WO90/10382 | 9/1990 | WIPO . |
| WO9105854 | 5/1991 | WIPO . |

OTHER PUBLICATIONS

Thorpe et al, "Section VIII, Fiber and Wood, Conifers", Handbook of plant cell culture, 1984, pp. 435–470.
Kyozuka et al, "Regeneration of Plants from Rice Protoplasts", Biotechnology in agriculture and forestry, vol. 8, 1992, pp. 109–123.
Collins et al., "Cell Culture and Somatic Cell Genetics of Plants", vol. 1 Laboratory Procedures and Their Applications, 1984, pp. 241–257.
George et al, "Plant Propagation by Tissue Culture", Handbook and Directory of Commercial Laboratories, 1984, pp. 213–223.
Bonga, "Clonal Propagation of Mature Trees: Problems And Possible Solutions", Cell and Tissue culture in Forestry vol. I, 1987, pp. 249–271.
Lelu et al, C. R. Acad. Sci., Paris, t.305, Serie III, pp. 105–109 (1987).
Attree et al, Can. J. Bot., vol. 68, pp. 30–34 (1990).
Van Engelen et al, TIG vol. 8(2), pp. 66–70 (1992).
Hohtola et al, Tree Physiology, vol. 8(4), pp. 423–428 (1991).
Arnold et al, Plantlet Regeneration in Vitro . . . in Norway Spruce (*Picea abies*), pp. 199–215.
Krogstrup, Biologia Plantarum 29:347–444 (1987).
Gupta et al, Can. J. For. Res., vol. 17, pp. 1130–1134 (1987).
Jansson et al, Physiol. Plant, 59:1–8 (1983).
Bornman, Biologia Plantarum, 27:249–256 (1985).
Tautorus et al, "Canadian Journal of Botany", vol. 68(8), pp. 1774–1779 (1990).
von Arnold, Forest Science, vol. 30(2), pp. 314–318 (1984).
Bekkauoui et al, Plant Cell Reports, vol. 6(6), pp. 476–479 (1987).
Thomas, Memories de la Societe Bontanique de France, pp. 147–178 (1973) (English Abstract).
Attree et al. 1990. Can. J. Bot. 68: 30–34.
Bekkaoui et al. 1987. Plant Cell Reports. 6:476–9.
Dunstan et al. 1987 New Phytol. 106:225–36.

*Primary Examiner*—David T. Fox
*Assistant Examiner*—Elizabeth C. Kemmerer
*Attorney, Agent, or Firm*—Cushman Darby & Cushman

[57] ABSTRACT

A method of producing embryogenic conifer callus, comprising culturing somatic tissue capable of growth derived from a conifer so as to form non-embryogenic callus and then culturing the non-embryogenic callus in the presence of a nurse culture so as to produce embryogenic callus. Embryogenic callus derived in this way can be used to produced plantlets by known techniques.

3 Claims, 1 Drawing Sheet

METHOD OF PRODUCING EMBRYOGENIC CALLUS OF NORWAY SPRUCE (*PICEA ABIES* AND REGENERATING PLANTLETS THEREFROM

This is a continuation of application Ser. No. 07/898,903, filed on Jun. 10, 1992.

FIELD OF THE INVENTION

This invention concerns the cultivation of conifers and relates to a method of producing embryogenic callus from conifer explants and a method of producing plantlets.

BACKGROUND OF THE INVENTION

Commercial forestry is concerned almost exclusively with conifers, especially trees of the Spruce genus (e.g. the Norway Spruce *Picea abies*), the Pine genus (e.g. the Loblolly pine, *Pinus taeda*), the Douglas Fir (*Pseudotsuga menziesii*) and the Larch (Larix sp.).

Their commercial significance has prompted much research into the cultivation and growth of such conifers. This research has been aided by the development of in vitro tissue culture systems, allowing for the cloning of selected strains.

At present, there are two main methods of producing multiple clones of coniferous trees.

One method, organogenesis, involves taking a suitable explant and cultivating the tissue in culture media containing carefully controlled nutrient and hormone levels, resulting in the formation of callus. This callus can then be placed on budding media. The resulting buds are separated and can be grown to form individual plantlets (as described by von Arnold, 1984).

The other method routinely employed is that of somatic embryogenesis, as disclosed by von Arnold & Hackman (1988) and by WO 91/05854. This method, less labour intensive than organogenesis, involves the formation in vitro of embryogenic callus from zygotic embryo explants. This callus gives rise to many proembryonic structures which can be separated and grown into plantlets.

However, somatic embryogenesis can only be performed using embryos or young cotyledon as starting materials. For example, success has been achieved with cotyledon explants from seven day old *Picea abies* seedlings (Lelu et al., 1984) and 30 day old seedlings of *Picea mariana* and *Picea galuca* (Attree et al., 1990) but not from older trees.

Similarly, organogenesis is fully successful only when the explant is taken from very young seedlings. When explants from older plants are used, it is possible to obtain adventitious buds, but these cannot be grown into plantlets (Jansson & Bornman, 1983; von Arnold, 1984).

This represents a problem because it is impossible to predict the quality of the mature tree from a young seedling or plantlet. Thus one might be cloning an inferior specimen. The present invention aims to overcome this problem.

SUMMARY OF THE INVENTION

In one aspect the invention provides a method of producing embryogenic conifer callus, comprising culturing somatic tissue capable of growth derived from a conifer so as to form non-embryogenic callus and then culturing said non-embryogenic callus in the presence of a nurse culture so as to produce embryogenic callus.

Typically the somatic tissue capable of growth is an explant taken from a needle, bud, shoot or root tissue.

This tissue may be taken from a mature tree, allowing for the selection of elite specimens for cloning. The age of the tree may vary for different species but the technique has been successfully performed using explants from a 26 year old specimen of *Picea abies*.

It is generally agreed by researchers in this field that the Norway Spruce (*Picea abies*) is the conifer which is hardest to cultivate. Thus, this technique is applicable to all conifers, but is particularly suitable for other species of Spruce (White, Black and Interior), the Douglas Fir, the Corsican Pine, Northern Pines and the Japanese and Europan Larch and hybrids thereof. As will be apparent, embryogenic callus obtained in this way can be used to obtain plantlets, e.g. by conventional growth techniques.

Nurse cultures are well known to those skilled in the art, being, for example used in transformation experiments. In a typical nurse culture embryogenic callus of juvenile origin and the non-embryogenic callus are located in close proximity on opposed sides of a microporous membrane such that there is no direct contact between the two calli and the only communication is via the pores of the membrane. Growth and maintenance of the calli is supported by a suitable culture medium.

Typically the pores of the membrane are 0.22 microns in diameter. The membrane might be nitrocellulose or other suitable material, as appreciated by those skilled in the art.

Preferably the nurse culture comprises embryogenic tissue of the same species as that from which the non-embryogenic callus is derived, but the nurse culture may be from a different strain or species as will be clear to those skilled in the art.

In another aspect the invention thus provides a method of producing plantlets, comprising culturing embryogenic callus produced by the method defined above in a suitable manner to produce plantlets.

Such media for this purpose are readily apparent to those skilled in the art.

In a further aspect the invention provides a method of producing conifer plantlets comprising culturing somatic tissue capable of growth derived from a conifer so as to form non-embryogenic callus; culturing said non-embryogenic callus in the presence of a nurse culture so as to form embryogenic callus; and culturing said embryogenic callus in a suitable manner so as to generate plantlets.

The invention may be better understood by reference to the following illustrative example and figure.

EXAMPLE

Figure 1:
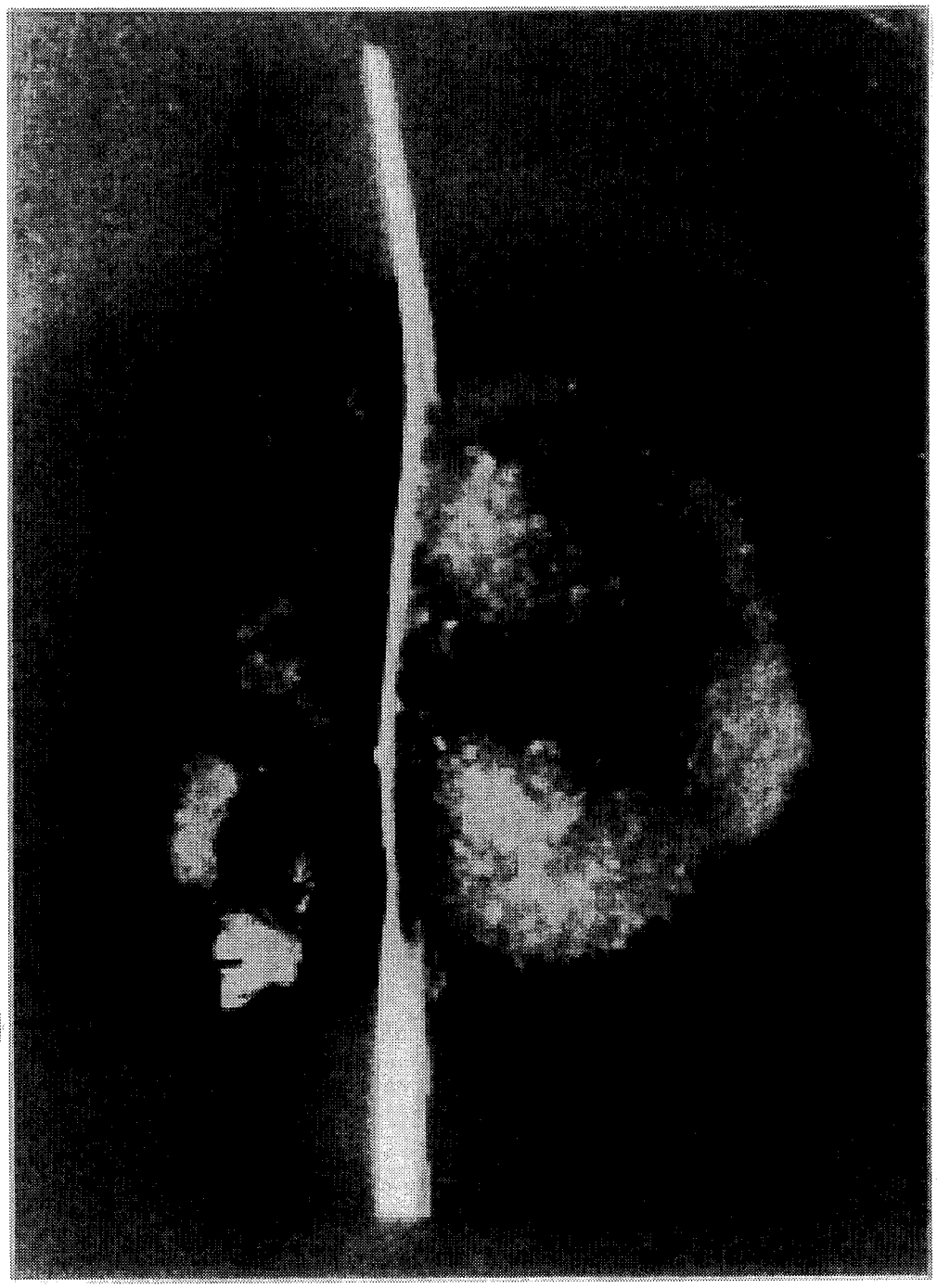
FIG. 1 shows a photograph of embryogenic callus produced by the method according to the invention.

Three sources were used to provide non-embryonic explants of Norway Spruce (*Picea abies*):

1. Axenic Shoot Cultures

These were the result of organogenesis from zygotic embryo explants after a 2 hour pulse with cytokinin (von Arnold and Hakman, 1988). Shoots that arose originally have been treated as clones and regularly transferred from 1988 onwards. They have been in free growth throughout and limited multiplication has occurred from axillary buds.

The original seed used was from a Henndorf provenance in Austria.

2. Six Year Old Trees

Five potted commercial seedlings, obtained from the Forestry Commission nursery in Scarborough, from an unknown provenance in Germany were used.

3. Cuttings from a Mature Tree

Several rooted cuttings from a provenance represented in IUFRO (International Union of Forestry Research Organisations) trials were used. This material had previously performed best in other tissue culture systems —for example, organogenesis from dormant buds. The provenance is Jilove n Prahy in Czechoslovakia and seedlings were planted in 1968 from 1964 seed collections. Mature trees were 26 years old at the time of the experiment described in this example. The explants taken thus cover three points in the maturation of Norway Spruce.

Culture Methods

The majority of explants were dormant needles ripped from shoots which had been previously surface sterilised from the six year old trees and cuttings. Sterilisation was not necessary from the shoots in culture. The concentration and duration of treatment in chlorox solutions was varied but was in always preceded with a dip in 70% ethanol. Many batches of needle explants were contaminated with fungi, often totally, irrespective of the sterilisation treatment. The explants consisting of a needle and a heel of stem tissue were placed on the media used routinely to establish and maintain embryogenic callus from zygotic embryos and gametophytes. Replication was from 20 to 1000 in various experiments. The medium used, termed ½ ES 7171 contained the following (in umoles per liter ), $KNO_3$ (8400 ) $MgSO_4$ $7H_2PO_4$ (1200). $CaCl_2.2H_2O$ (520), $NH_4NO_3$ (15000).$ZnSO_4.7H_2O$ (5), $MnSO_4.4H_2O$ (5) $H_3BO_3$ (5) KI (2.3), $Na_2MoO_4$. $5H_2O$ (0.05), $CuSO_4.5H_2O$ (0.008), $COCl_2.6H_2$ (0.008), $Na_2EDTA.2H_2O$ (0.03) $FeSO_4.7H_2O$ (0.03), Mesoinitositol (500) Nicotinic Acid (0.8) Thiamine (1.4) Pyrodoxine HCl (0.5) Glycine (2.6) Glutamine (0.002) Naphylacetic acid (10) Benzylaminopurine (5) plus 88 m moles of Sucrose and 0.8% Difco Agar.

Embryonic shoot explants were also used as explants from the mature tree dissected from dormant vegetative buds. Explants were transferred regularly each six weeks to the same medium as was any resultant callus. Nurse cultures were established from calli after six transfers or more from establishment. These constitute an embryogenic callus from zygotic embryo explants from seed of a Gerlitz provenance (which can be routinely induced to produce somatic embryos) and a needle or bud callus physically separated by a 0.22 u millipore filter membrane as shown in FIG. 1. The same media were used throughout. Nurse cultures were transferred each four weeks with great care not to mix the two calli. All cultures were maintained at 22° C. in darkness.

Table 1 summarises the number of explants which produced callus after three transfers. All callus arose from the stem heel end of needles and clearly from Table 1 the age of the plant from which explants were taken influenced the ability to callus. The bud explants taken directly from the 26 year old tree were more productive than needle explants from rooted cuttings. During subsequent transfers the number of calli declined until, at transfer six, 98 of the 139 axenic shoot cultures which originally produced callus remained. 2 of the 6 year old trees had no explants with callus and 51 of the 180 calli from the 26 year old tree survived. Nurse cultures were established of a representative sample at this point and later after 8 to 10 transfers embryogenic musilaginous sectors appeared in eight cultures representative of 3 of the axenic shoot culture clones and all those of the 6 year old trees which had surviving calli. Shown in FIG. 1, embryogenic callus 10 is easily distinguished as fast growing and spreading in growth habit. Its identity was confirmed by the presence of proembryos and suspensor-like cells after staining and light microscopy. All the new embryogenic callus has been isolated away from the original non-embryogenic material. Nurse cultures allowed non-embryogenic callus to survive as only six calli representing two of the axenic shoot culture clones were transferred after twelve passages. However, 19 of the same lines were active as nurse cultures and 26 of the original 180 calli from 26 year old material were transferred. None of this material has produced embryogenic sections up to transfer 15. One of the six surviving axenic shoot culture calli has produced embryogenic sectors after transfer 15 (18 months) without the use of a nurse culture.

Somatic embryogenesis is favoured by the use of explants from the youngest tissue available. However, the results presented here show that at low frequency embryogenic callus can be produced from explants from older trees. The nurse cultures employed promoted growth and survival of the slow growing callus obtained from older trees and, although not essential, considerably promoted the formation of the embryogenic callus. The most productive group of explants was from the 6 year old trees with 5 of the 96 nurse cultures established resulting in embryogenic callus production.

One major limiting factor from older tissues is the low frequency of original callusing, particularly from needles, which is compounded by the unreliability of surface sterilisation of explants from trees grown outside. Bud explants, although more productive, are destructive to the original tree. Another important limit is the time required to maintain cultures for more than 12 months. There is a balance to the time allowed as calli are dying at a high rate shown by the fact that only material from 2 of the original 139 axenic shoot culture clones survived 12 transfers. The period of 6 transfers before attempts to induce embryogenesis were made was deliberate to allow cell divisions in a disorganised state to occur which could eliminate the mature status of the tissue. Nurse cultures aided survival of calli and it could be argued promoted embryogenesis. Although physically separated the nurse and non-embryogenic callus are in intimate chemical contact and there are several candidates for active promoting molecules such as some isoforms of peroxidase (van Engelen & de Vries, 1992) and arabinoglulactan proteins (EP-A-91810315.1).

TABLE 1

| Age of Tree in 1990 | Type of Explant | No. of Explants | No. with Callus | % % | Genotypes Used |
|---|---|---|---|---|---|
| 2 (oxenic culture shoots) | Needle | 2920 | 2277 | 77.9 | 146 (139 genotypes with callus) |
| 6 | Needle | 1440 | 212 | 14.7 | 5 |
| 26 | Needle (ex cuttings) | 1212 | 2 | 0.2 | 1 |
|  | Buds | 3120 | 180 | 5.7 | 1 |

References

S. von Arnold, (1984). Importance of genotype on the potential for in vitro adventitious bud production of *Picea abies*.

S. von Arnold and I. Hakman (1988). Plantlet regeneration in vitro via adventitious buds and somatic embryos in Norway Spruce (*Picea abies*) in: Genetic manipulation of woody plants (eds. J. W. Hanover and D. E. Keathley), 199– 219.

S. M. Attree, S. Budimir and L. C. Fowke. Somatic embryogenesis and plantlet regeneration from cultured shoots and cotyledons of seedlings from store seeds of black and white spruce (*Picea mariana* and *Picea glauca*). Can. J. Bot., 68 30–34.

J. M. Bonga (1987). Clonal propagation of mature trees. Problems and possible solutions. In Cell and Tissue Culture in: Forestry (eds. J. M. Bonga, D. J. Durzan). Martinus Nijhoff. Vol. 1, 249–272.

F. A. van Engelen and S. C. de Cries (1992). Extracellular proteins in plant embryogenesis. T.I.G., 8, (2), 66–70.

D. K. Gupta, D. J. Durzan and B. J. Finkle (1987). Somatic polyembryogenesis in embryogenic cell masses of *Picea abies* (Norway Spruce) and *Pinus taeda* (Loblolly Pine) after thawing from liquid nitrogen. Can. J. For.Res., 17, 1130–1134.

E. Jansson and C. H. Bornman (1983). Morphogenesis in dormant embryonic shoots of *Picea abies*. Influence of the crown and cold treatment. Physical Plant, 59, 1–8.

M-A. Lelu, M. Boulay and Y. Arnold. Obtention de cals embryogenes a partir de cotyledons de *Picea abies* (L) Karst preleves sur de jeunes plantes agees de 3 a 7 jours apres germination. C.R. Acad. Sci. Paris, 305, III, 105–109.

I claim:

1. A method of producing embryogenic Norway spruce callus, comprising culturing needle or bud explants from Norway spruce trees approximately 26 years old or younger so as to form non-embryogenic callus and culturing said non-embryogenic callus in the presence of Norway spruce nurse cells so as to produce embryogenic callus, wherein said non-embryogenic callus and said nurse cells are located in close proximity on opposed sides of a filter membrane.

2. A method of producing Norway spruce plantlets, comprising culturing embryonic callus produced by the method of claim 1, in a suitable manner to produce plantlets.

3. The method according to claim 1 for producing embryogenic Norway spruce callus, wherein said needle explants are from Norway spruce trees 6 years old or younger and wherein said filter membrane is a 0.22 micron millipore filter membrane.

* * * * *